(12) United States Patent
Nishiyama et al.

(10) Patent No.: US 6,618,850 B2
(45) Date of Patent: Sep. 9, 2003

(54) INSPECTION METHOD AND INSPECTION SYSTEM USING CHARGED PARTICLE BEAM

(75) Inventors: Hidetoshi Nishiyama, Kokubunji (JP); Mari Nozoe, Hino (JP); Hiroyuki Shinada, Chofu (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/785,275

(22) Filed: Feb. 20, 2001

(65) Prior Publication Data

US 2001/0016938 A1 Aug. 23, 2001

(30) Foreign Application Priority Data

Feb. 22, 2000 (JP) ........................................ 2000-050501
Sep. 7, 2000 (JP) ........................................ 2000-276640

(51) Int. Cl.[7] .............................................. G06F 17/50
(52) U.S. Cl. .............................. 716/20; 716/19; 716/21
(58) Field of Search .............................. 716/20, 21, 19

(56) References Cited

U.S. PATENT DOCUMENTS 5,640,539 A * 6/1997 Goishi et al. ................. 716/21
6,195,773 B1 * 2/2001 Wada ......................... 714/724
6,204,075 B1 * 3/2001 Kikuchi ....................... 438/18

FOREIGN PATENT DOCUMENTS

| JP | 59-155941 | 9/1984 |
|---|---|---|
| JP | 5-258703 | 10/1993 |
| JP | 6-326165 | 11/1994 |
| JP | 7-288096 | 10/1995 |
| JP | 8-160109 | 6/1996 |
| JP | 11-121561 | 4/1999 |

* cited by examiner

*Primary Examiner*—Vuthe Siek
*Assistant Examiner*—Brandon Bowers
(74) *Attorney, Agent, or Firm*—Mattingly, Stanger & Malur, P.C.

(57) ABSTRACT

Secondary electrons and back scattered electrons generated by irradiating a wafer to be inspected, such as a semiconductor wafer, with a charged particle beam are detected by a detector. A signal proportional to the number of detected electrons is generated, and an inspection image is formed on the basis of this signal. On the other hand, in consideration of a current value and irradiation energy of a charged particle beam, an electric field on the surface of the inspection wafer, emission efficiency of the secondary electrons and back scattered electrons, and the like, an electric resistance and an electric capacitance are determined so as to coincide with those in the inspection image. In a state where a difference between a resistance value in a normal portion and a resistance value in a defective portion is sufficiently increased by using the charging generated by the irradiation of electron beams, an inspection is thereby conducted to detect a defect.

6 Claims, 14 Drawing Sheets

DEFECT

DEFECT

INSPECTION METHOD AND INSPECTION SYSTEM USING CHARGED PARTICLE BEAM

BACKGROUND OF THE INVENTION

The present invention relates to a method and system for manufacturing a wafer having a fine circuit pattern such as a semiconductor device, or liquid crystal. More particularly, the invention relates to a technique of inspecting a pattern of a semiconductor device or a photomask, and to an inspecting method and system using a charged particle beam, for inspecting a defect in an arbitrary part on an unfinished semiconductor wafer in a semiconductor device fabricating process.

A semiconductor device is manufactured by, for example, repeating a step of transferring a pattern formed with a photomask on a semiconductor wafer by a lithography process and an etching process. In a manufacturing step of a semiconductor device, whether the lithography process, etching process, and the like are successfully performed or not exerts a large influence on the yield of the semiconductor device. It is consequently important to detect occurrence of an abnormal state or a failure at an early stage or before it occurs. Particularly, to improve the yield, it is important to measure electric resistance and electric capacitance of a contact hole and an interconnection in a partially finished semiconductor wafer at an early stage of the manufacturing process. There are the following conventional techniques of performing inspections to detect an electrical defect.

One of the techniques is a nano-probe device JP-A No. H8-160109) for measuring electric resistance by making a sharpened tungsten (W) needle (with the tip having a radius of curvature of about 0.1 $\mu$m) come into direct contact with a measurement portion. As patterns become finer in recent years, however, the size of a portion to be measured becomes about the same or smaller than that of the W needle, so that the measurement is becoming very difficult. As means for dealing with the problem, it can be considered to reduce the radius of curvature of the tip of the W needle. In this case, however, the tip becomes very soft and is consequently deformed when it comes into contact with the portion to be measured. The method is not a realistic one. Another problem is contact resistance. When the needle and the portion to be measured are made of different materials, especially, one of them is made of a semiconductor, a Schottky junction occurs, and electric resistance depending on a voltage occurs in the portion. Consequently, accurate measurement cannot be performed.

Another conventional technique uses a SEM (Scanning Electron Microscope) and is disclosed in JP-A No. H5-258703, JP-A No. H11-121561, and JP-A No. H6-326165.

According to the technique disclosed in JP-A No.H5-258703, an image to be inspected is compared with an adjacent image, and a portion having different potential contrast (brightness) is determined as a defect, thereby detecting a defect. The technique, however, does not have means for obtaining and displaying electric characteristics (electric resistance and electric capacitance) and, therefore, cannot determine whether the portion is critical or not.

According to the technique disclosed in JP-A No. H11-121561, the degree of emission of secondary electrons is controlled by a control electrode positioned on a wafer, the surface of the wafer is charged positively or negatively, and a normal portion, a low-resistance defective portion, and a high-resistance defective portion are determined from a voltage contrast image obtained at this time.

Control of the emission of secondary electrons by the control electrode is disclosed in JP-A No. S59-155941. For example, in a voltage contrast image obtained in the case where the control electrode is adjusted to be positively charged, a low-resistance defective portion (for example, low resistance of few hundreds $\Omega$) is light, a high-resistance defective portion (electric resistance: $\infty$) is dark, and a normal portion is light but is darker than the low-resistance defective portion since the normal portion has resistance higher than the low-resistance defective portion. From the lightness/darkness of the image, the resistance can be determined to be high or low, but an absolute value cannot be calculated. By measuring a leak current, electric resistance can be calculated. However, it takes time for the inspection and the electric resistance cannot be measured at high speed.

According to the technique disclosed in JP-A No. H6-326165, an interconnection on a substrate is irradiated with electron beams, a dielectric current is generated between the substrate and the ground by charges generated by the irradiation, and a change with time is measured. Although the electric capacitance can be measured to be large or small, an absolute value cannot be measured.

In an inspection using such a voltage contrast image of the SEM, in some cases, a difference in potential contrast between the normal portion and the defective portion is small depending on the structure of a wafer, and it is difficult to detect a defect. For example, in the case where a circuit has a pn junction, when the pn junction is reverse-biased by charges which are generated in association with irradiation of electron beams, the portion becomes high-resistant. Due to this, it is difficult to discriminate the portion from a high-resistant portion with faulty electrical continuity.

As described above, since the nano-probe device has a problem such that a portion to be measured is smaller than the tip of the needle and a problem of the contact resistance between the needle and a sample, accurate electric resistance cannot be measured depending on a sample. It takes very long time to inspect the whole face of a wafer and is substantially impossible to conduct the inspection. Although an apparatus using the SEM can determine whether the electric resistance is high or low and whether the electric capacitance is large or small from a voltage contrast image but cannot estimate an absolute value. Although a resistance value can be calculated by measuring a leak current, it takes time for an inspection, the inspection cannot be conducted at high speed, and it takes very long time to inspect the whole face of a wafer. Further, depending on the structure of a wafer (for example, when a pn junction is formed), it is difficult to discriminate a normal portion from a defective portion in a voltage contrast image.

SUMMARY OF THE INVENTION

An object of the invention is to provide an inspection method and system for automatically calculating values of electric resistance and electric capacitance and obtaining distributions and tendencies of electric resistance and electric capacitance of the surface of a substrate such as a wafer in short time only by acquiring a voltage contrast image. Another object is to provide appropriate inspection parameters corresponding to the structure of a wafer.

The inventors of the present invention have found that the objects can be achieved by using the fact that a charged particle beam image (voltage contrast image) obtained by irradiating a sample with a charged particle beam depends on electric resistance and electric capacitance between the irradiation region and the ground and irradiation time.

The mechanism will be described by referring to FIG. 2. Electrons are used as an example of particles applied. It is assumed that an incident energy EPE is about 500 eV where emission efficiency σ of the sum of secondary electrons and back scattered electrons is larger than 1. Usually, an electron having energy equal to or smaller than 50 eV is called a secondary electron and an electron having energy larger than 50 eV is called a back scattering electron. When an insulator 60 is irradiated with an electron beam, an electron beam irradiated region 61 is charged positively (a case where it is charged at 4V is shown as an example), and a potential barrier of Us [eV] is formed on the surface.

Consequently, as shown by an energy ESE distribution of the sum NSE of the number of secondary electrons and back scattered electrons of FIG. 3, the secondary electrons and back scattered electrons having energy lower than Us are not emitted. Even when the secondary electrons and back scattered electrons are emitted, they are returned to the insulator side. When the number of electrons returned is $N_1$, the number of emitted electrons is $N_2$, and the ratio of the secondary electrons and back scattered electrons which are not returned but are emitted is $\sigma_{SE}$, $\sigma_{SE}=N2/(N_1+N_2)$. A substantial emission efficiency $\sigma_{eff}$ is expressed as $\sigma_{eff}=\sigma_{SE}\times\sigma$. With the irradiation of electron beams, the charging voltage increases and the ratio of returned secondary electrons and back scattered electrons becomes higher. Consequently, $\sigma_{eff}$ gradually decreases and, finally, stability is achieved with a charging voltage at which $\sigma_{eff}$ is 1.

On the other hand, in the case of a conductor having sufficiently low electric resistance, electrons can be supplied. The charging is therefore lessened, and a and $\sigma_{eff}$ are almost equal to each other. The insulator looks dark and the conductor looks light.

An example by which the inventors of the present invention have found that electric resistance can be measured by using the above fact will now be described. A sample used is a wafer as shown in FIG. 4 in which an $SiO_2$ film 402 is formed on a silicon (Si) 407 and contact holes 401 in each of which a tungsten (W) plug 400 (having a diameter of 0.25 μm) is buried are opened. Each plug has electric resistance due to a residue 403 of $SiO_2$ (402) on the bottom of the plug. Reference numeral 404 shows a high-resistant open defect having the residue 403, and 405 denotes a low-resistant short defect in which plugs are connected.

An equivalent circuit shown in FIG. 5 including an electric resistor R and an electric capacitor C of an electron carrying path was used. From the shape of the plug, the electric capacitance C was set to $10^{-17}$ F (farad). Electron irradiation parameters in FIG. 23 were used. 10 keV was set as the initial energy of an electron beam 19 emitted from an electron gun 10, an earth voltage was applied to a retarding electrode 63, and a retarding voltage of −9.5 kV was applied to a wafer 9 to be inspected. Consequently, the incident energy EPE of the electron beam to the wafer was 500 eV.

As a result, it was found that the sum NSE of the number of secondary electrons and back scattered electrons to be detected changes with time as shown in FIG. 6. The vertical axis denotes the value obtained by dividing NES to be detected by electron beam current IP [A], and the horizontal axis indicates the product of electron beam irradiation time Te (or time required for a scan electron beam to cross the plug) and IP. It was also found that the relation between NSE which was stabilized after elapse of sufficient time and the electric resistance R is as shown in FIG. 7. The vertical axis indicates NSE/IP and the horizontal axis indicates the product of R and IP. In order to calculate the electric resistance R, a change in NSE is necessary.

From the above, the inventors of the present invention have found for the first time that the parameter of the current IP of the electron beam to calculate the electric resistance R is 0<log(R·IP) <3. Although the graph of FIG. 7 depends on the shapes of material and sample, the change amount is very small. By changing the retarding voltage $V_R$ or charging (voltage $V_B$) the peripheral region of a plug by applying an electron beam before inspection, the NSE can be changed as shown in FIGS. 8 and 9, so that high-sensitive inspection parameters exist. In order to confirm the calculation prediction, each of plugs was irradiated with an electron beam and the number of secondary electrons and back scattered electrons from the plug were detected.

After that, the electric resistance of each plug was measured by a nano-prober. Since the uppermost layer of the plug is made of W, the contact resistance with the W needle of the nano-prober is sufficiently low. FIG. 10 shows the dependency on the electric resistance R of the NSE obtained as a result. The vertical axis indicates the quotient of the NSE and the beam current IP, and the horizontal axis denotes the product between the electric resistance R and the beam current Ip. In the graph, a solid line shows calculation and circles indicate experiment. It was found that the calculation and the experiment coincides with each other. That is, it was found that the resistance value can be calculated from the voltage contrast image by calculating the dependency on resistance of the sum of the number of secondary electrons and back scattered electrons.

It was also found that the electric capacitance can be also measured by using the semiconductor wafer. This will be described hereinbelow. The beam current IP was set to 100 nA. A plug having resistance $10^{12}$·(ohm) or higher recognized by the nano-prober method was used. By comparing the result of calculation of a change in NSE to be detected which is obtained by changing irradiation time of the electron beam (or time required for the electron beam to cross the plug) with the calculation result, the electric capacitance was estimated from the comparison result. As shown in FIG. 11 of the experiment result and the calculation result, the change with time of the NSE when the electric capacitance was set to $10^{-17}$ F (farad) in the calculation result reproduces the experiment result almost faithfully. The value is almost equal to the value calculated from the shape of the plug or the like.

Further, a method of providing appropriate inspection parameters adapted to the structure of a wafer will now be described. FIG. 8 shows that the NSE changes by changing the retarding voltage $V_R$. In this case, the charging voltage US(V) in an electron beam irradiation region also varies as shown in FIG. 24. The phenomenon is used for the inspection. For example, when a circuit pattern having a pn junction is irradiated with an electron beam and the pn junction is charged so as to be reverse-biased, the junction has high resistance, and it is consequently difficult to discriminate the junction from a defect of faulty electrical continuity. However, by changing the retarding voltage to increase the charging voltage and to cause a breakdown in the pn junction, the resistance value can be reduced. Since the difference between the resistance value in the normal portion and the resistance value in the defective portion becomes large and the normal portion and the defective portion become different from each other in a voltage contrast image, the inspection can be conducted in such a state.

In the case where the pn junction itself has a defect and the resistance value in the reverse bias direction is small, the retarding voltage is adjusted to a charging state where a breakdown is caused only in the defective pn junction. The difference between the resistance value in the normal portion and the resistance value in the defective portion is increased, and a difference occurs between the normal and defective portions, so that the inspection can be conducted. Although the retarding voltage is used here, also by changing other electron irradiation parameters such as electron beam current, incident energy of the electron beam to a sample, irradiation time, and the number of irradiation times, similar effects can be produced.

It was found that, by the methods as described above, the electric resistance and electric capacitance can be estimated and the appropriate defect detecting parameters adapted to the structure of a wafer can be provided. Although the electron beam was used in the examples, the similar effects can be produced by using other charged particle beams such as positive ions and negative ions.

In an actual inspection system, the electric resistance and electric capacitance are determined automatically as follows.

First, a semiconductor wafer is scanned with a charged particle beam once or a plurality of times. Scan time may be changed. Secondary electrons and back scattered electrons generated are detected by a detector, a signal proportional to the number of electrons detected is generated, and an inspection image corresponding to the scan is formed on the basis of the signal.

Subsequently, by a computer such as a work station or personal computer, in consideration of the current value of the charged particle beam, irradiation energy, scan time, the number of scanning times, electric field on the surface of the semiconductor wafer, emission efficiency of the secondary electrons and back scattered electrons, and the like, an image is formed by using the electric resistance and electric capacitance as parameters. The electric resistance and electric capacitance are determined so that the image coincides with the inspection image.

In the inspection, by changing the current value of the charged particle beam, the measurement range of the electric resistance can be changed. As a process before acquiring an image, the charged particle beam of a predetermined quantity is preliminarily applied or the retarding voltage is applied to the semiconductor wafer, thereby enabling measurement sensitivity to be changed.

Appropriate inspection parameters adapted to the structure of a wafer can be also provided.

DETAILED DESCRIPTION OF THE PREFERRED EMBODIMENTS

First Embodiment

Figure 1:
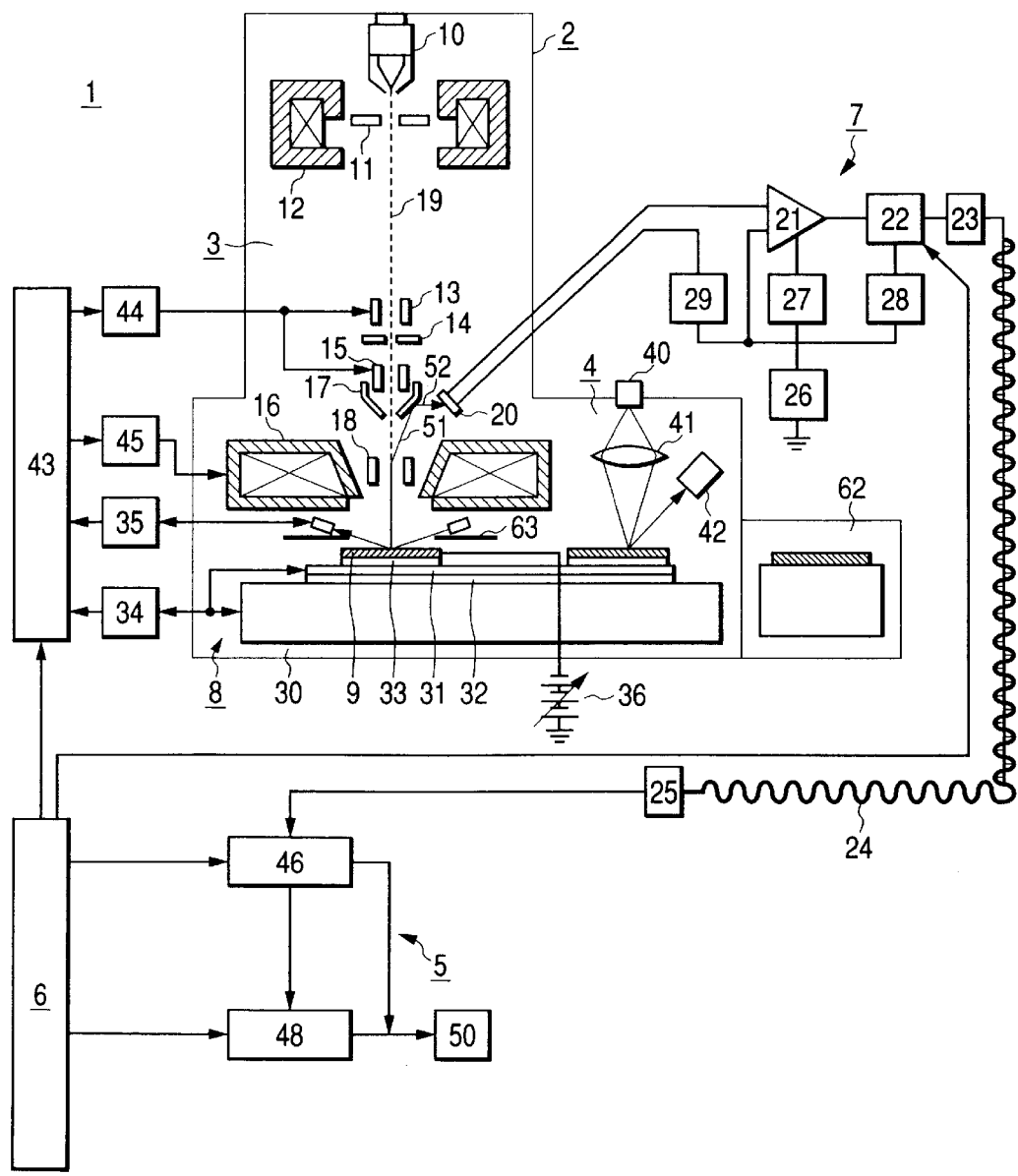
FIG. 1 is a block diagram showing an inspection system according to an embodiment of the invention.
Figure 2:
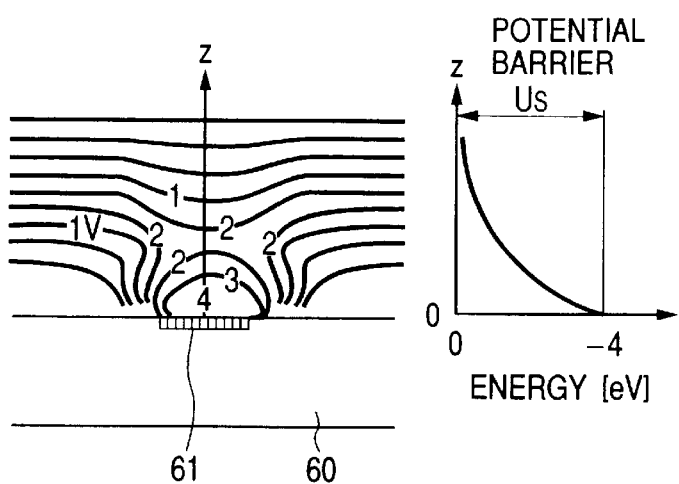
FIG. 2 is a diagram showing a state where the surface of a wafer is charged and a potential barrier is formed in association with irradiation of electron beams.
Figure 3:
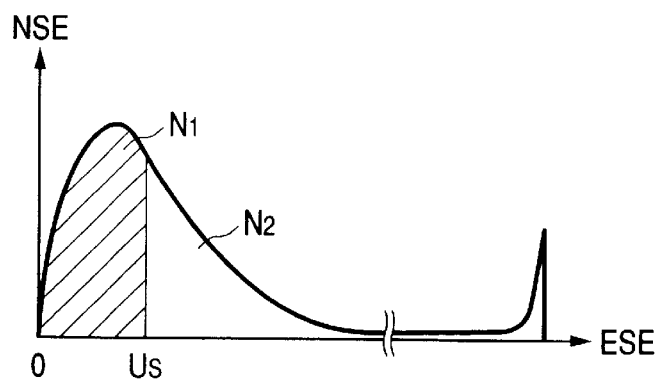
FIG. 3 is a diagram showing an energy ESE distribution of a sum NSE of the number of secondary electrons and back scattered electrons.

FIG. 1 shows the configuration of an inspection system as a first embodiment of the invention. The inspection system 1 has an inspection chamber 2 evacuated to be in a vacuum, and a spare chamber (not shown in this embodiment) for carrying a wafer 9 to be inspected into the inspection chamber 2. The spare chamber can be evacuated independent of the inspection chamber 2. The inspection system 1 has, other than the inspection chamber 2 and the spare chamber, a control unit 6 and an image processing unit 5. The inspection chamber 2 has therein, broadly, electron optics 3, a detector 7, a sample chamber 8, and an optical microscope unit 4.

The electron optics 3 include an electron gun 10, an electron beam extraction electrode 11, a condenser lens 12, a blanking deflector 13, a scanning deflector 15, an aperture 14, an objective lens 16, a converter electrode 17, and an EXB deflector 18. In the detector 7, a detector 20 is disposed above the objective lens 16 in the inspection chamber 2. An output signal of the detector 20 is amplified by a preamplifier 21 installed on the outside of the inspection chamber 2 and is converted by an AD converter 22 into digital data. The sample chamber 8 includes a sample holder 30, an x stage 31, a y stage 32, a rotation stage 33, a stage position measurement unit 34, and a wafer height measure sensor 35.

The optical microscope unit 4 is mounted in a position near but sufficiently apart from the electron optics 3 in the inspection chamber 2 so as not to exert an influence on each other. The distance between the electron optics 3 and the optical microscope unit 4 is known. The x stage 31 or y stage 32 reciprocates in the known distance between the electron optics 3 and the optical microscope unit 4. The optical microscope unit 4 has a white light source 40, a light lens 41, and a CCD camera 42. The image processing unit 5 includes an image memory unit 46 and a calculator 48. An electron beam image or optical image acquired, and measured electric resistance and electric capacitance are displayed on a monitor 50.

Operation commands and operation parameters of the units in the system are inputted/outputted from the control unit 6. The parameters such as acceleration voltage on generation of an electron beam, electron beam deflection width, deflection speed, signal capturing timing of detector, and sample holder moving speed are preliminarily entered to the control unit 6 so as to be optionally or selectively set according to the purpose. The control unit 6 monitors a deviation in position and height from signals of the stage position measurement unit 34 and the wafer height measure sensor 35 by using a correction control circuit 43, generates a correction signal on the basis of the monitoring result, and sends the correction signal to an objective lens power supply 45 and a scanning signal generator 44 so that the correct position is always irradiated with the electron beam. To acquire an image of the surface of the inspection wafer 9, the inspection wafer 9 is irradiated with the narrowed electron beam 19 to thereby generate secondary electrons and back scattered electrons 51, and the secondary electrons and back scattered electrons 51 are detected synchronously with the scanning of the electron beam 19 and the movement of the stages 31 and 32.

In the electron gun 10, a thermal electric field emitting electron source of a diffusion supply type is used. By using the electron gun 10, a stabler electron beam current as compared with conventional electron sources such as a tungsten (W) filament electron source and a cold emission type electron source can be assured. Consequently, a voltage contrast image with little fluctuation in brightness can be obtained. The electron beam 19 is emitted from the electron gun 10 by applying a voltage between the electron gun 10 and the extraction electrode 11. The electron beam 19 is accelerated by applying a negative potential of a high voltage to the electron gun 10.

The electron beam 19 travels toward the sample holder 30 with an energy corresponding to the potential, is condensed by the condenser lens 12, further narrowed by the objective lens 16, and is incident on the inspection wafer 9 (wafer having a fine circuit pattern, such as a semiconductor wafer, chip, liquid crystal, or mask) mounted on the x-stage 31 and the y-stage 32 on the sample holder 30.

A scanning signal generator 44 for generating a scanning signal and a blanking signal is connected to the blanking deflector 13, and the objective lens power supply 45 is connected to each of the condenser lens 12 and the objective lens 16. A negative voltage (retarding voltage) can be applied from a retarding power supply 36 to the inspection wafer 9. By adjusting the voltage of the retarding power supply 36, a primary electron beam is decelerated, and an electron beam irradiation energy to the inspection wafer 9 can be adjusted to an optimum value without changing the potential of the electron gun 10.

The secondary electrons and back scattered electrons 51 generated by irradiating the inspection wafer 9 with the electron beam 19 are accelerated by the negative voltage applied to the wafer 9. The EXB deflector 18 is disposed over the inspection wafer 9 and the accelerated secondary electrons and the back scattered electrons 51 are deflected by the EXB deflector 18 to a predetermined direction. In accordance with the voltage applied to the EXB deflector 18 and the intensity of the magnetic field, the deflection amount can be adjusted. The electromagnetic field can be varied interlockingly with the negative voltage applied to the sample. The secondary electrons and back scattered electrons 51 deflected by the EXB deflector 18 collide with the converter electrode 17 under predetermined conditions. When the accelerated secondary electrons and back scattered electrons 51 collide with the converter electrode 17, secondary electrons and back scattered electrons 52 are generated from the converter electrode 17.

The detector 7 has the detector 20 in the evacuated inspection chamber 2, and the preamplifier 21, the AD converter 22, a converter 23, an optical fiber 24, a converter 25, a high voltage power supply 26, a preamplifier power supply 27, an AD converter power supply 28, and a power supply 29 which are on the outside of the inspection chamber 2. As described above, the detector 20 in the detector 7 is disposed above the objective lens 16 in the inspection chamber 2. The detector 20, preamplifier 21, AD converter 22, converter 23, preamplifier power supply 27, and AD converter power supply 28 are floated at a positive potential by the high voltage power supply 26. The secondary electrons and back scattered electrons 52 generated by the collision with the converter electrode 17 are led to the detector 20 by a suction field.

The detector 20 is constructed to detect the secondary electrons and back scattered electrons 52 interlockingly with the timing of scanning the electron beam 19, which are generated by the collision of the secondary electrons and back scattered electrons 51 generated when the inspection wafer 9 is irradiated with the electron beams 19. An output signal of the detector 20 is amplified by the preamplifier 21 mounted on the outside of the inspection chamber 2 and converted to digital data by the AD converter 22. The AD converter 22 immediately converts the analog signal detected by the detector 20 and amplified by the preamplifier 21 and sends the digital signal to the image processing unit 5. Since the detected analog signal is converted to a digital signal immediately after the detection and the digital signal is transmitted, a signal having a high S/N ratio can be obtained at high speed. As the detector 20, for example, a semiconductor detector may be used.

The inspection wafer 9 is mounted on the x and y stages 31 and 32. At the time of inspection, either a method of two-dimensionally scanning the inspection wafer 9 with the electron beam 19 while the x and y stages 31 and 32 are kept still or a method of linearly scanning the inspection wafer 9 with the electron beam 19 in the x direction so that the x and y stages 31 and 32 are continuously moved at constant speed in the y direction at the time of inspection can be selected. In the case of inspecting a specific relatively small region, the former method of carrying out the inspection by keeping the stages still is effective. In the case of inspecting a relatively large region, the method of carrying out the inspection while continuously moving the stages at constant speed is effective. When it is necessary to blank the electron beam 19, the electron beam 19 is deflected by the blanking deflector 13 so as not to pass through the aperture 14.

As the stage position measurement unit 34, a measurement unit using laser interference is employed in the embodiment. The positions of the x and y stages 31 and 32 can be monitored in a real-time manner and can be transferred to the control unit 6. Data such as rotational speeds of the motor for the x and y stages 31 and 32 and also the rotation stage 33 is similarly transferred from their drivers to the control unit 6. The control unit 6 can accurately grasp the region and the position irradiated with the electron beam 19 on the basis of the above data. As necessary, a positional deviation of the irradiation position of the electron beam 19 is corrected in a real-time manner by the correction control unit 43. The region irradiated with the electron beam 19 can be stored every inspection wafer.

The wafer height measure sensor 35 takes the form of an optical measure sensor as a measure system which does not use an electron beam. For example, a laser interference measure sensor or a reflection type measure sensor for measuring a change in the position of reflection light is used. The wafer height measure sensor 35 measures the height of the inspection wafer 9 mounted on the x and y stages 31 and 32 in a real-time manner. In the embodiment, a method of irradiating the inspection wafer 9 with elongated white light which has passed through a slit through a transparent window, detecting the position of reflection light by the position detecting monitor, and calculating a change amount of the height from a fluctuation in position is used. On the basis of the measurement data of the wafer height measure sensor 35, the focal distance of the objective lens 16 for narrowing the electron beam 19 is dynamically corrected and the electron beam 19 with the focal point in a non-inspection region can be always emitted. A warp and a distortion in height of the inspection wafer 9 are preliminarily measured before irradiation of the electron beam. It is also possible to set correction parameters of each inspection region of the objection lens 16 on the basis of the measured data.

The image processing unit 5 is constructed by the image memory unit 46, calculator 48, and monitor 50. An image signal of the inspection wafer 9 detected by the detector 20 is amplified by the preamplifier 21, and converted by the AD converter 22 to a digital signal. The digital signal is converted by the converter 23 into a light signal. The light signal is transmitted via the optical fiber 24, and converted again to an electric signal by the converter 25. The electric signal is stored in the image memory unit 46.

The electron beam irradiation parameters for forming an image and various detection parameters of the detection system are preset at the time of setting inspection parameters, and registered in files in a database. The calculator 48 reads the image signal supplied to the image memory unit 46, calculates the correspondence between the above-described image signal level and a surface charging voltage on the basis of the electron beam irradiation parameters, and calculates the electric resistance and electric capacitance corresponding to the image signal level. The monitor 50 displays the electric resistance and electric capacitance calculated by the calculator 48 and/or the image stored in the image memory unit 46.

Figure 4:
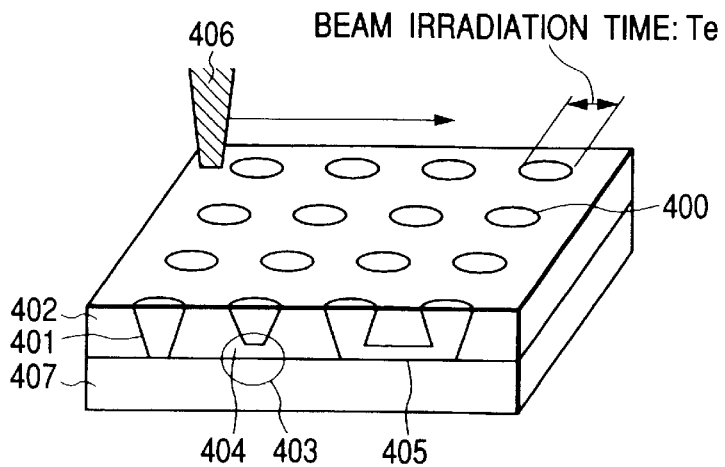
FIG. 4 is a schematic diagram showing a cross-sectional structure of a semiconductor wafer.
Figure 5:
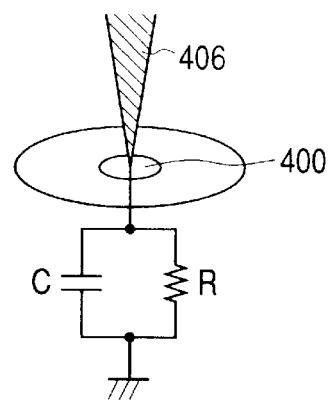
FIG. 5 is a diagram showing an example of an equivalent circuit of a contact hole in FIG. 4.
Figure 6:
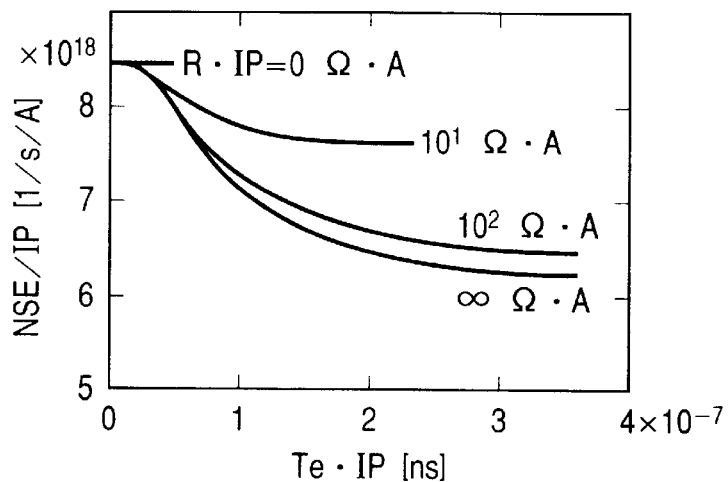
FIG. 6 is a diagram showing a change with time in the sum NSE of the number of secondary electrons and back scattered electrons to be detected.
Figure 12:
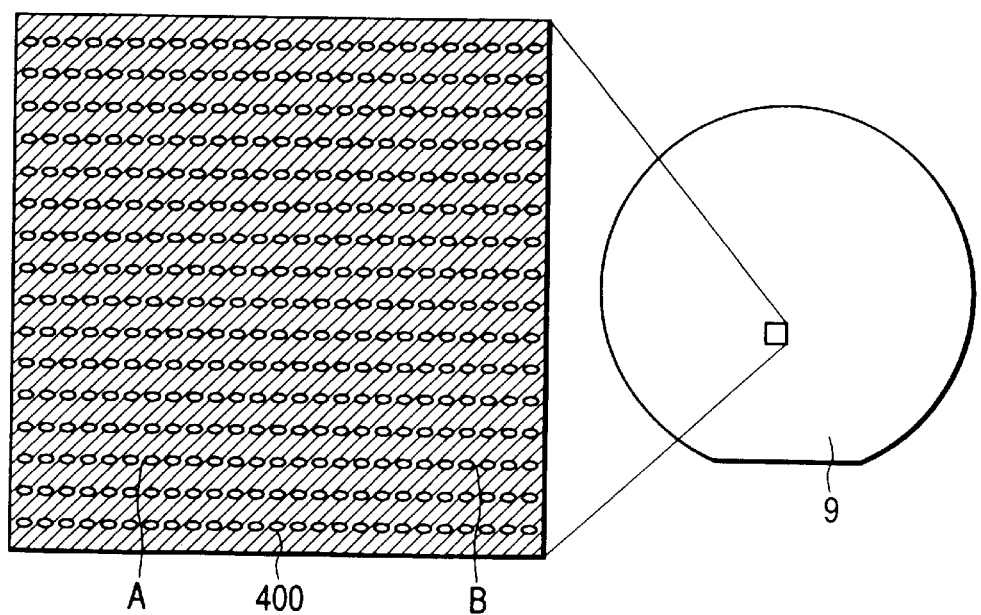
FIG. 12 is a diagram showing a semiconductor wafer and a voltage contrast image used in First Example.

An action in the case of measuring the electric resistance and electric capacitance of, for example, a partly-finished semiconductor wafer (having a similar cross-sectional structure as that of FIG. 4) of 300 mm$\phi$ shown in FIG. 12 as the inspection wafer 9 by the inspection system 1 will now be described. First, although not shown in FIG. 1, a semiconductor wafer is loaded by inspection wafer carrying means into a sample exchange chamber where the inspection wafer 9 is mounted on the sample holder and held and fixed. After that, the sample exchange chamber is evacuated to a certain degree of vacuum. The inspection wafer 9 is transferred to the inspection chamber 2 for an inspection. In the inspection chamber 2, the inspection wafer 9 mounted on the sample holder is held and fixed on the sample holder 30, x and y stages 31 and 32, and rotation stage 33.

The set inspection semiconductor wafer 9 is disposed in predetermined first coordinates below the optical microscope 4 by moving the x and y stages 31 and 32 in the X and Y directions on the basis of the pre-registered predetermined inspection parameters. An optical microscope image of the circuit pattern formed on the inspection wafer 9 is monitored by the monitor 50 and is compared with an equivalent circuit pattern image in the same position prestored for position rotation correction, thereby calculating a position correction value for the first coordinates. The inspection wafer 9 is moved away from the first coordinates by a predetermined distance to second coordinates where a circuit pattern equivalent to that in the first coordinates exists. Similarly, an optical microscope image is observed and is compared with a circuit pattern image stored for position rotation correction, thereby calculating a position correction value of the second coordinates and a rotation deviation amount with respect to the first coordinates. The rotation stage 33 is rotated by the calculated rotation deviation amount to correct its rotation amount.

Although the rotation deviation amount is corrected by rotating the rotation stage 33 in the embodiment, it can be also corrected by a method of correcting a scanning deflection position of the electron beam on the basis of the calculated rotation deviation amount without using the rotation stage 33. In the optical microscope image observation, a circuit pattern which can be observed by not only an optical microscope image but also an electron beam image is selected. For the position correction in the future, the first coordinates, positional deviation amount of the first circuit pattern by the optical microscope image observation, second coordinates, and positional deviation amount of the second circuit pattern by the optical microscope image observation are stored and transferred to the control unit 6.

Further, an image observed by the optical microscope is used, the circuit pattern formed on the inspection wafer 9 is observed, the positions of chips and the distance between chips in the circuit pattern on the inspection wafer 9, the pitch of repetitive patterns such as memory cells, and the like are preliminarily measured, and measurement values are supplied to the control unit 6. A chip to be inspected on the inspection wafer 9 and a region to be inspected in the chip are set on the basis of an image of the optical microscope and are supplied to the control unit 6 in a manner similar to the above. An image of the optical microscope can be observed at a relatively low magnification. When the surface of the inspection wafer 9 is covered with, for example, a silicon oxide film, the underlayer can be also observed through the film. Consequently, the array of chips and the layout of circuit patterns in a chip can be easily observed and the region to be inspected can be easily set.

After completion of the predetermined correcting work and the preparing work such as setting of the region to be inspected by using the optical microscope unit 4 as described above, by moving the x and y stages 31 and 32, the inspection wafer 9 is moved under the electron optics 3. When the inspection wafer 9 is disposed under the electron optics 3, works similar to the correcting work and the setting of the inspection region performed by the optical microscope unit 4 are carried out by using an electron beam image. In this case, the electron beam image is acquired as follows.

On the basis of the coordinate values stored and corrected in the positioning using the optical microscope image, the same circuit pattern as that observed by the optical microscope unit 4 is two-dimensionally scanned in the XY directions and irradiated with the electron beam 19 by the scanning deflector 44. By the two-dimensional scanning with the electron beam, the secondary electrons and back scattered electrons 51 generated from the portion to be observed are detected by the configuration and action of the above-described units for detecting electrons, thereby obtaining an electron beam image. Since the simple and easy inspection position recognition, positioning, position adjustment, and also rotation correction have been carried out by using the optical microscope image, positioning, position correction, and rotation correction can be performed with high accuracy at higher resolution and higher magnification as compared with the optical image.

When the inspection wafer 9 is irradiated with the electron beam 19, the irradiated position is charged. The charging sometimes distorts an image, so that it exerts an adverse influence on the inspection. In order to avoid the influence of the charging at the time of inspection, in a preparing work before the inspection such as the position rotation correction or inspection region setting, as a circuit pattern to be irradiated with the electron beam 19, it is arranged to automatically select either a circuit pattern existing on the outside of the inspection region or an equivalent circuit pattern on a chip other than the inspection chip from the control unit 6. By the arrangement, the influence of the electron beam 19 emitted by the preparing work before the inspection is not exerted on the inspection image at the time of inspection.

Figure 13:
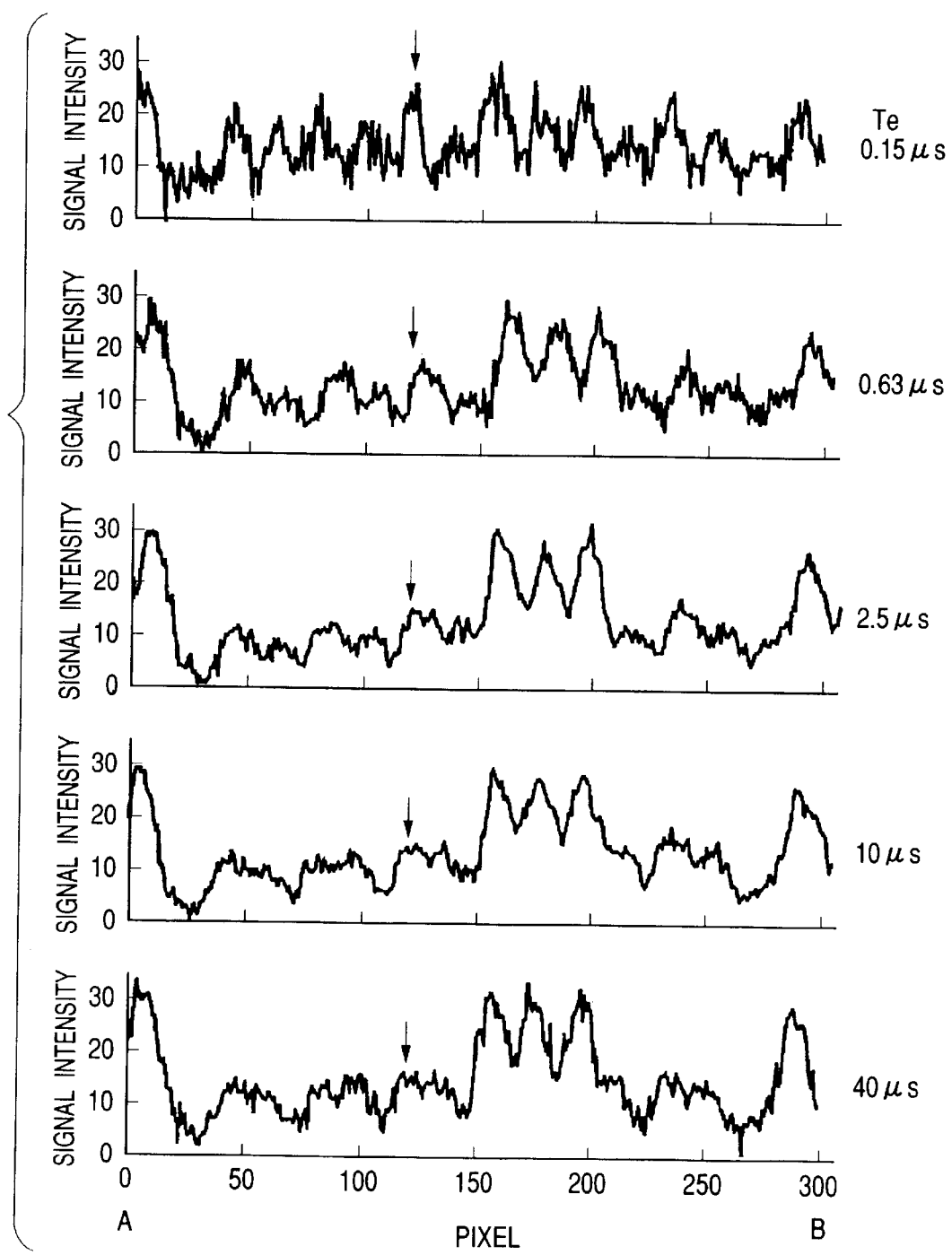
FIG. 13 is a diagram showing potential contrast signals of the semiconductor wafer in FIG. 12.

Subsequently, in an arbitrary region on the inspection wafer, electric resistance and electric capacitance are measured. An image is obtained with incident energy of 500 eV and an electron beam current of 100 nA. FIG. 13 shows signals of the secondary electrons and back scattered electrons generated between A and B of plugs 400 linearly arranged as shown in FIG. 12 in the obtained image. In graphs in FIG. 13, time Te of application of beams on the plugs varies from 0.15 to 40 $\mu$s. Although some peaks decrease with the electron irradiation time Te, stable signals are obtained with sufficiently long Te (2.5 $\mu$s or longer in this case).

Figure 7:
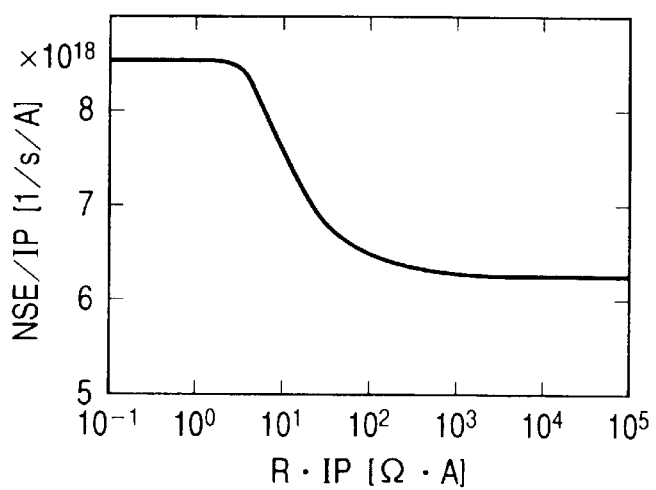
FIG. 7 is a diagram showing the dependency on electric resistance R of the sum NSE of the number of secondary electrons and back scattered electrons to be detected.
Figure 14:
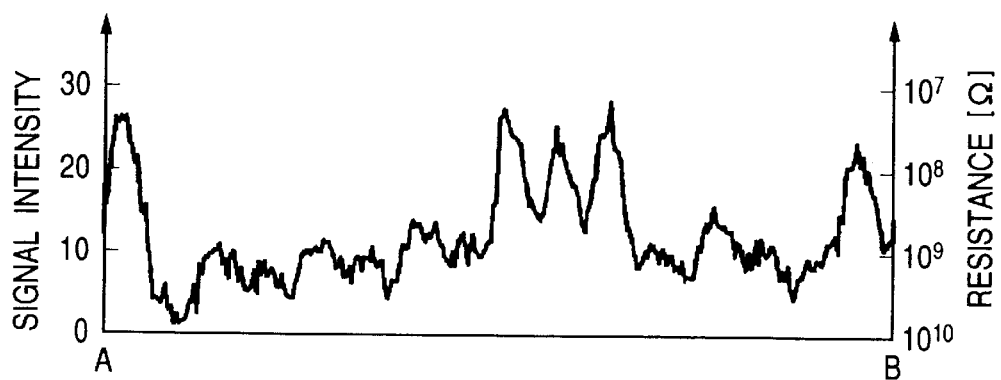
FIG. 14 is a diagram showing the potential contrast signal of FIG. 13 and a calculated electric resistance value.
Figure 15:
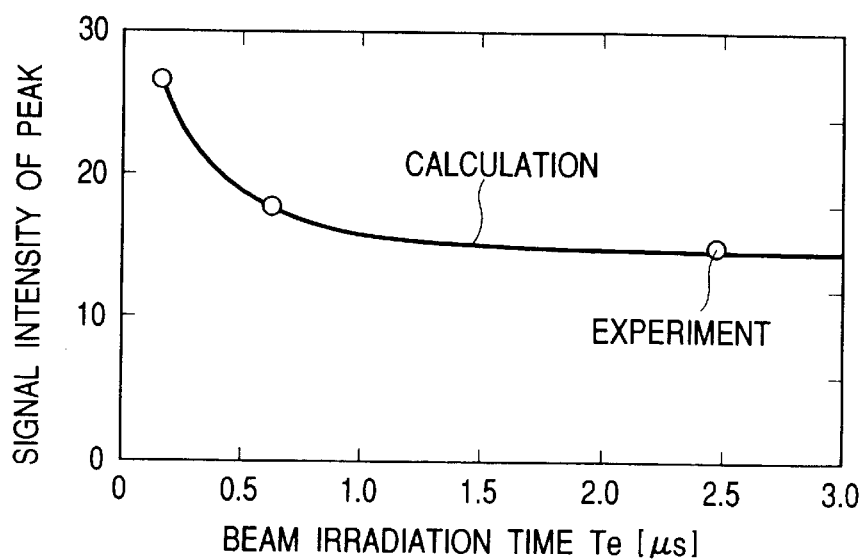
FIG. 15 is a diagram showing a change in time of irradiating beams having peak intensities indicated by the arrows in FIG. 13.

When the electric resistance was derived from a result of calculation as described with reference to FIG. 7 under such circumstances, values (right vertical axis) in the range from $10^7$ to $10^{10}$ $\Omega$ (ohm) as shown in FIG. 14 were obtained. After that, the electric capacitance was calculated from the change in electron irradiation time Te at the peaks shown by the arrows in FIG. 13. When the electric capacitance was calculated from the relation between the intensity of the peak and Te shown in FIG. 15, a value of $10^{-17}$ F (farad) was obtained. By repeating the operation, the electric resistance and electric capacitance were measured with respect to all of selected inspection regions.

Figure 8:
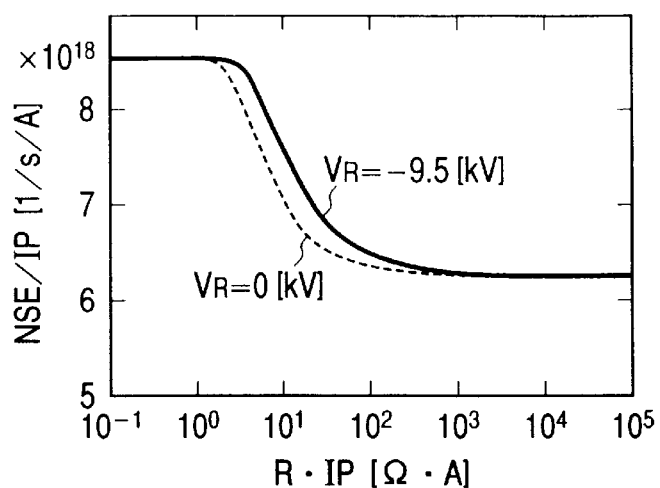
FIG. 8 is a diagram showing the dependency on the electric resistance R of the sum NSE of the number of secondary electrons and back scattered electrons to be detected when a retarding voltage $V_R$ is changed.
Figure 9:
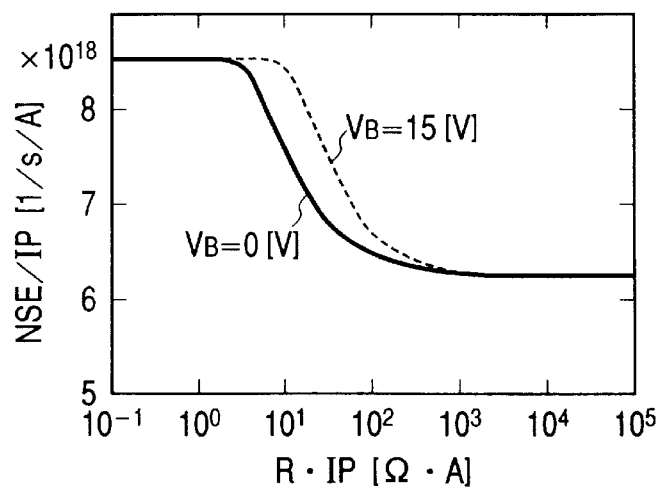
FIG. 9 is a diagram showing dependency on the electric resistance R of the sum NSE of the number of secondary electrons and back scattered electrons to be detected when a charging voltage VB around a plug is changed.
Figure 10:
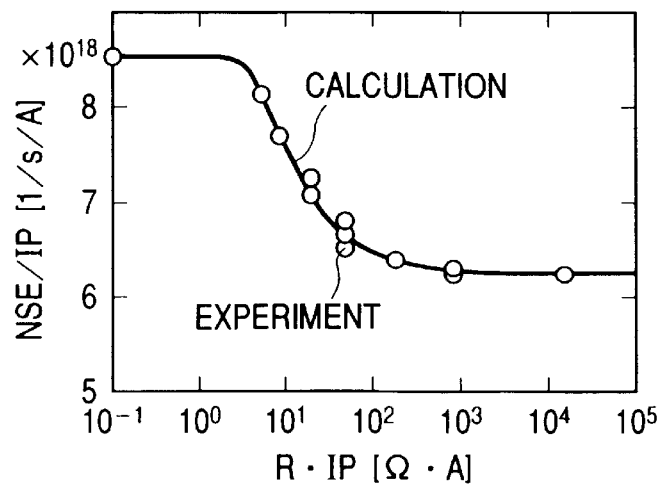
FIG. 10 is a diagram showing a comparison between calculation and experiment of the dependency on the electric resistance R of the sum NSE of the number of secondary electrons and back scattered electrons to be detected.
Figure 11:
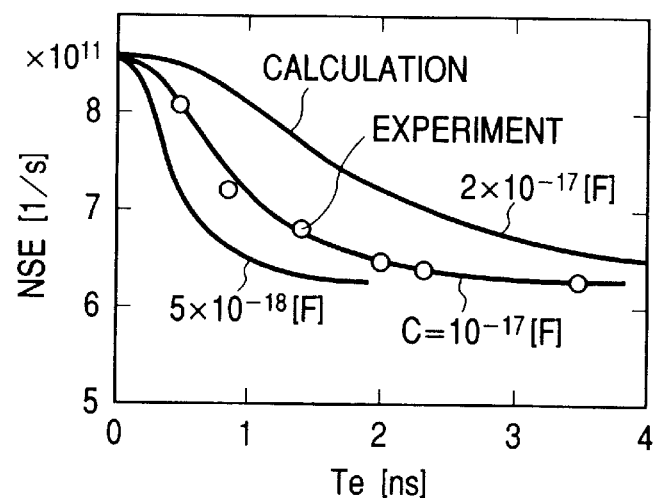
FIG. 11 is a diagram showing a comparison between calculation and experiment of a change with time of the sum NSE of the number of secondary electrons and back scattered electrons to be detected.

In the system, by changing the retarding voltage or preliminarily charging an insulated portion to a certain degree by irradiation of electron beams before acquiring an image, a potential generated in front of the plug is changed and, therefore, the sensitivity of resistance measurement can be changed as shown in FIGS. 8 and 9. It is understood from FIG. 8 that, by decreasing the retarding voltage, the measurement range can be narrowed. It is understood from FIG. 9 that, by charging the insulated portion, the measurement range can be narrowed. Although the electron beam was used here as the charged particle beam, when an ion beam is used instead of the electron beam, similar measurement can be performed.

Second Embodiment

In a second embodiment, the electron beam image is acquired by using the inspection system described in the first embodiment and stored in the image memory unit 46. Images of neighboring equivalent circuit patterns are compared with each other by the calculator 48. When a differential signal level is higher than a predetermined value, the portion in the electron beam image is recognized as a defective portion and is displayed. Since the system has been described in detail in the first embodiment, the description will not be repeated. From the image signal level in the defective position, the electric resistance and capacitance are calculated by the calculator 48. The degree of difference in resistance or capacitance of the defective portion from the normal portion is obtained. There are the following three methods of obtaining an image of the defective portion.

In a first method, an inspection of comparing the images with each other is conducted. After completion of the inspection, an image is obtained again in the defect occurrence coordinates under the same parameters as those in the inspection. The electric resistance and capacitance are calculated from the obtained image.

In a second method, in a manner similar to the first method, after completion of the inspection, an image is obtained again in the defect occurrence coordinates under electron beam parameters different from those in the inspection, and the electric resistance and capacitance of the defective portion are calculated from the correspondence of the image signal level with the image acquisition parameters. In the second method, as the image acquisition parameters different from those for the inspection, the beam current, scan speed, the number of irradiation times, or the like is changed. An image may be acquired while changing one of the parameters or a plurality of parameters to calculate the electric resistance and capacitance.

In a third method, an image determined as defective in an inspection is automatically stored, an image signal in the defective portion is read, and calculation is executed. In this case, it is unnecessary to obtain an image again in the defective portion after completion of the inspection.

Figure 16A:
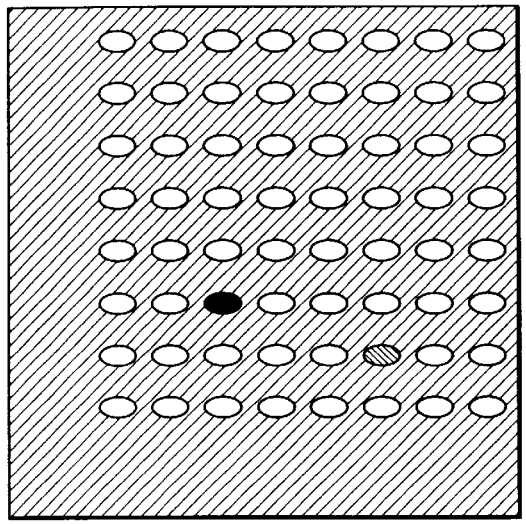
FIGS. 16(a) and 16(b) are diagrams showing inspection images 1 obtained in Second Example.
Figure 16B:
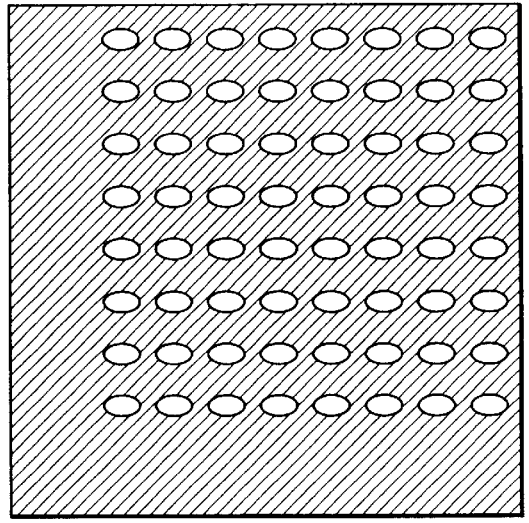
Figure 17:
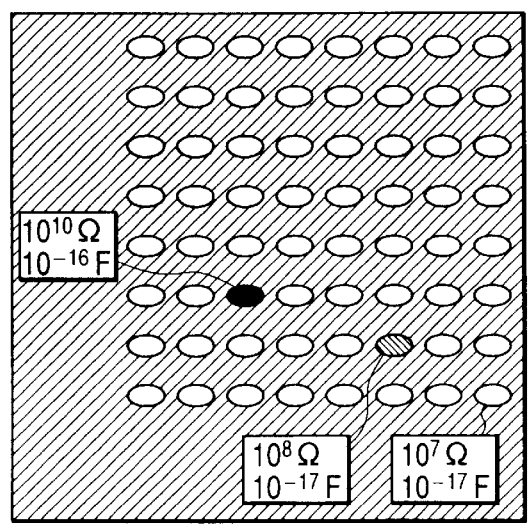
FIG. 17 is a diagram showing an inspection image 2 obtained in Second Example.

An example of the inspection method of carrying out the inspection in the second embodiment and displaying the electric defect level of the defective portion will be described. As an example, FIG. 16(a) shows a circuit pattern including a defective portion after carrying out the inspection of a semiconductor wafer having 300 mm$\phi$, and FIG. 16(b) shows an equivalent circuit pattern adjacent to the circuit pattern of FIG. 16(a). When arbitrary defects in the circuit pattern are specified from the screen, the image of defective portions is displayed as shown in FIG. 17 and, simultaneously, the electric resistance R and the electric capacitance C of each of the defective portions are displayed (a defective portion (1) of $10^{10}$ $\phi$ and $10^{-16}$ F and a defective portion (2) of $10^8$ $\Omega$ and $10^{-17}$ F). As references, the electric resistance ($10^7$ $\Omega$) and the electric capacitance ($10^{-17}$ F) of a normal portion can be similarly displayed.

The kind of each of the defective portions can be determined from the electric resistance R and the electric capacitance C. For example, since the resistance R and capacitance C in the defective portion (1) are higher than the references, it is determined that the defective portion (1) is completely non-conductive due to a residual film. Since the resistance R is higher than the reference resistance while no change occurs in the capacitance, it is determined that the portion (2) is defective due to deficiency of the plug material buried in the contact hole.

Third Embodiment

A third embodiment relates to an inspection method and inspection system for detecting, as a defect, a circuit pattern having resistance different from a predetermined resistance, which is derived from the brightness of an image by obtaining an electron beam image, and simultaneously comparing the brightness of the image in the circuit pattern position with predetermined brightness by using the inspection system described in the first embodiment.

Figure 18:
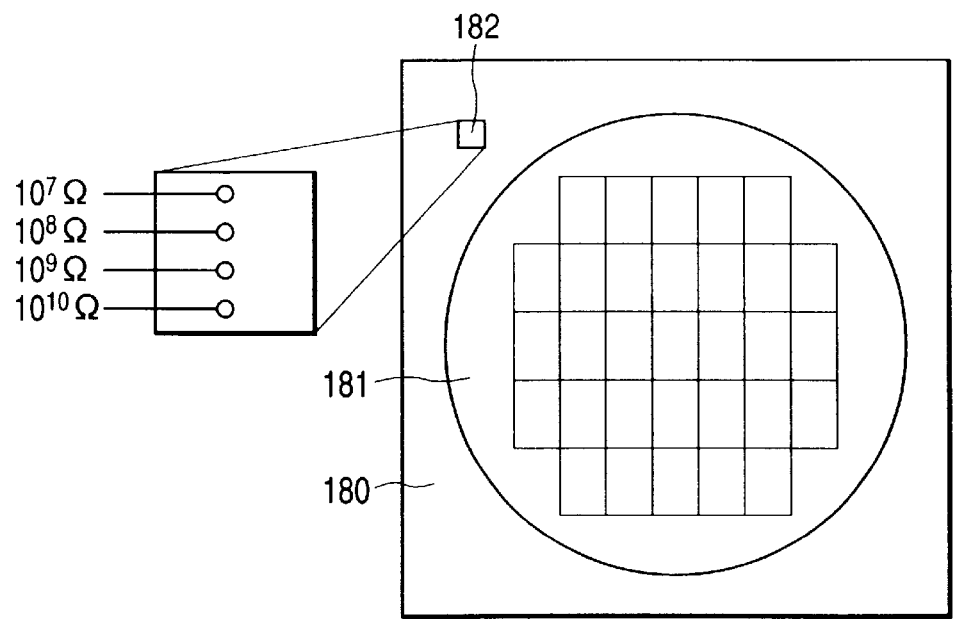
FIG. 18 is a diagram showing a sample holder with a standard resistance sample used in Third Example.

First, in FIG. 18, a wafer 181 to be inspected is loaded into the inspection system, and pre-registered electron beam irradiation parameters and signal detection parameters are set. On a sample holder 180, a standard sample 182 of which resistance under predetermined electron beam parameters is preliminarily calculated is attached. Before starting the inspection, an image of the standard sample 182 is acquired, and the correspondence between the resistance and capacitance and the electron beam image signal level is calibrated.

On the basis of a design value of the resistance or capacitance of the inspection wafer 181, a predetermined permissible level range is determined and set. After that, an electron beam image of an arbitrary region in the inspection wafer 181 is obtained. An image brightness signal obtained at the time of the inspection is compared with the set permissible level. A circuit pattern having brightness out of the permissible level is recognized and detected as a defect.

Fourth Embodiment

Figure 19:
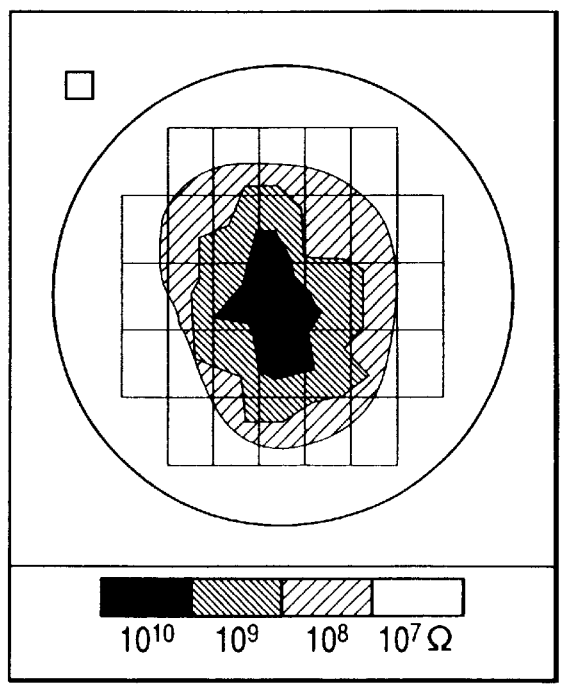
FIG. 19 is a diagram showing an inspection image obtained in Fourth Example.

A fourth embodiment relates to an inspection method and inspection system for calibrating the correspondence between the electron beam image brightness and the electric resistance and capacitance by the method described in the third embodiment by using the system described in the first embodiment, acquiring an electron beam image of a set arbitrary region, and changing colors according to the levels of resistance or displaying the levels of resistance by contour lines. FIG. 19 shows an example of an inspection result. By changing colors according to the resistance levels or displaying contour lines, a distribution of the resistance absolute levels is derived.

Fifth Embodiment

A fifth embodiment relates to an example of irradiating a predetermined circuit pattern with an electron beam under the condition that the pattern is not scanned with an electron beam by using the system described in the first embodiment and measuring the electric resistance and electric capacitance from a change in the signal level of the circuit pattern. In the embodiment, by measuring a change with time in the sum NSE of the number of secondary electrons and back scattered electrons emitted from an arbitrary region in the inspection wafer 9 and detected, the electric resistance and the electric capacitance are estimated. For this purpose, first, as a pre-process, a region around the arbitrary region is scanned with the narrowed electron beams 19 and a voltage contrast image is obtained.

Figure 20:
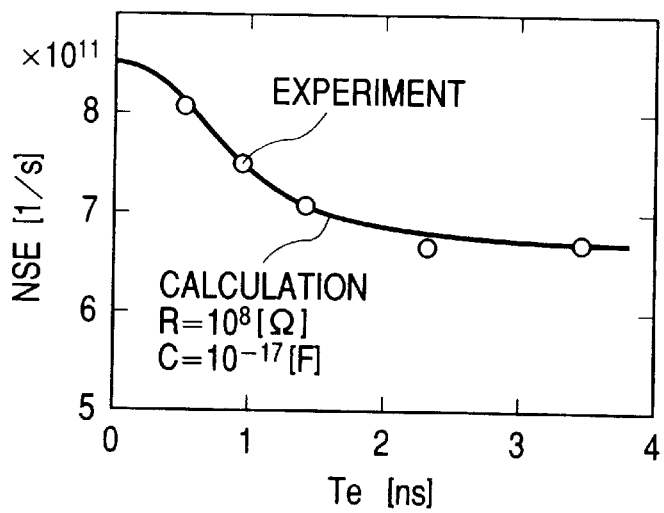
FIG. 20 is a diagram showing experiments and calculated values of a change with time in the sum of secondary electrons and back scattered electrons to be detected, which are obtained in Fifth Example.

After that, from the image, a deflection parameter for irradiating the arbitrary region with an electron beam is set, the electron beam is applied with the parameter, and a change with time in the sum NSE of the number of secondary and back scattered electrons detected is obtained. FIG. 20 shows the result obtained at this time. The value matches well with the result of calculation using the electric resistance of $10^8$ $\Omega$ and the electric capacitance of $10^{-17}$ F. In such a manner, the electric resistance and electric capacitance can be determined.

Sixth Embodiment

Figure 21:
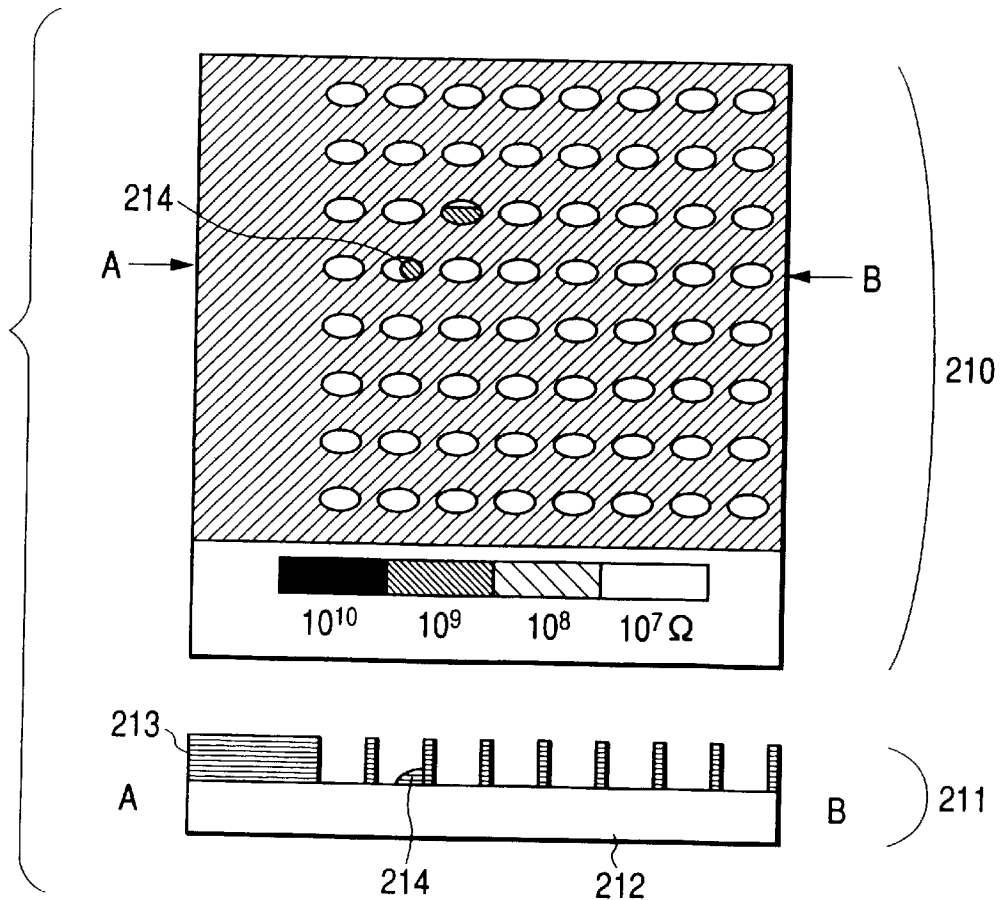
FIG. 21 is a diagram showing an inspection image obtained in Sixth Example.

A sixth embodiment relates to a method and system for inspecting, for example, a residue 214 of a resist 231 on a semiconductor wafer 212 by using the system described in the first embodiment. According to the inspection method and system, the correspondence between the electron beam image brightness and the electric resistance and capacitance is calibrated by the method described in the third embodiment, an electron beam image of a set arbitrary region is acquired, and the residue is displayed in place of resistance level. FIG. 21 shows an inspection image 210, and an expected cross section image 211 of a wafer between A and B in the inspection image 210. In accordance with the degrees of the reside 214, colors may be changed or contour lines can be displayed.

Seventh Embodiment

Figure 22:
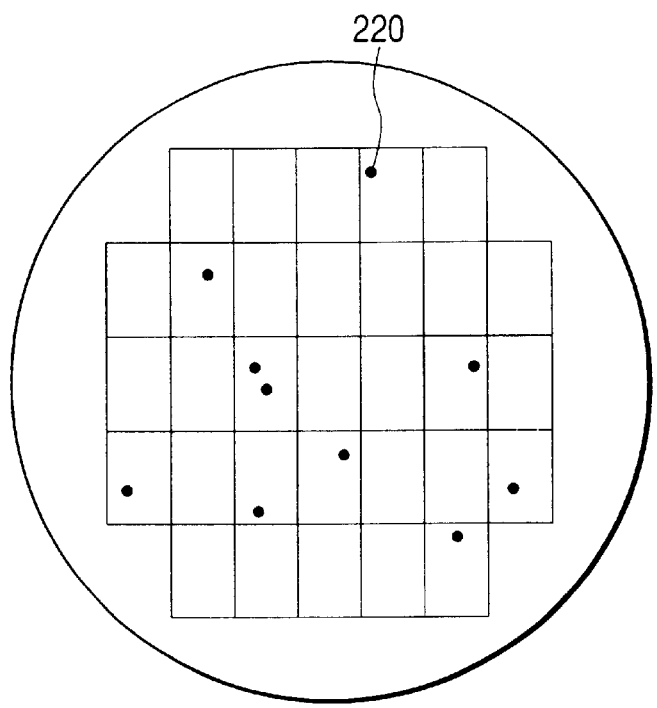
FIG. 22 is a diagram showing an inspection image obtained in Seventh Example.
Figure 23:
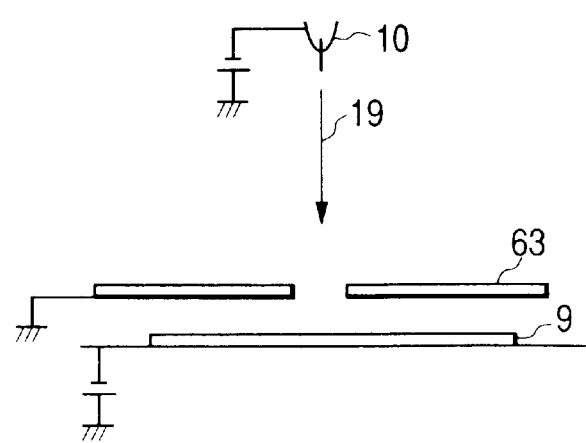
FIG. 23 is a diagram showing an example of electron beam irradiating parameters.

A seventh embodiment relates to a method and system for inspecting the whole face of a semi-finish semiconductor wafer having 300 mm$\phi$ on which a circuit is formed by using the system described in the first embodiment. FIG. 22 shows the result of the inspection on the whole surface of the wafer in a few hours by the method described in the second embodiment. A portion having resistance of $10^8$ $\Omega$ or higher is displayed as a defect 220.

Eighth Embodiment

An example of providing appropriate inspection parameters in the case where an electric resistance value of a pattern has dependency on voltage in the circuit pattern defect inspection (for example, a case where a pn junction portion or a Schottky junction portion is formed) will be described.

Figure 25:
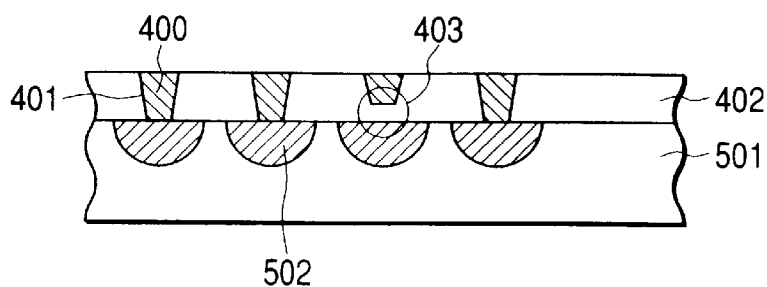
FIG. 25 is a diagram showing a cross section of a wafer in which a contact hole having a pn junction is formed.
Figure 26:
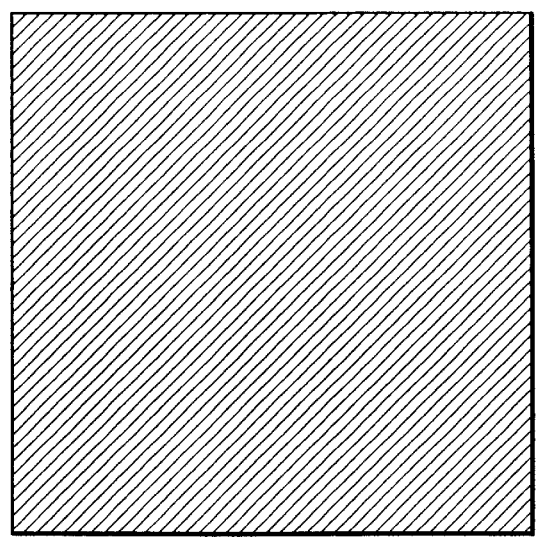
FIG. 26 is a diagram showing a voltage contrast image when a retarding voltage is not proper.

FIG. 25 is a cross section showing an example of contact holes each having a pn junction (502 denotes a p-Si and 502 indicates an n-Si). An inspection of poor conduction of such a contact hole was conducted by using an electron beam (IP=100 nA) of incident energy of 500 eV. FIG. 26 shows a voltage contrast image when the retarding voltage is 0V. The potential contrast of the contact hole is too low to discriminate a defective portion.

Figure 27:
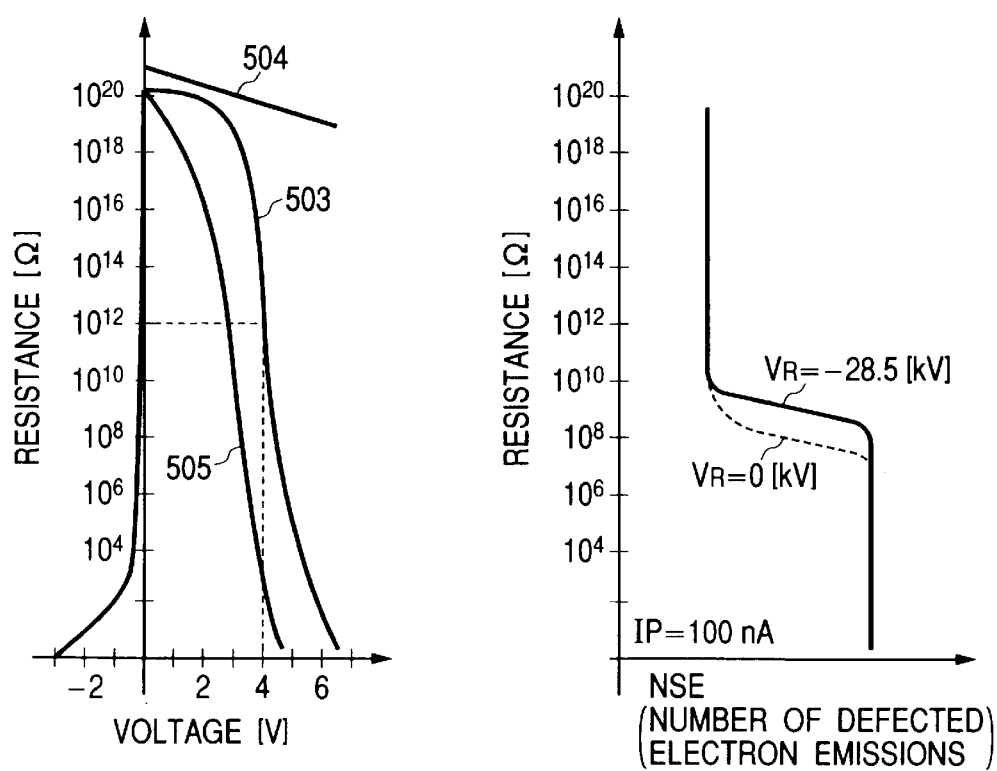
FIG. 27 is a diagram showing the resistance of a pn junction as a function of a voltage.

In order to clarify the cause, resistance on voltage of a normal contact hole and that of a contact hole with a residue were measured. The left graph in FIG. 27 shows the result. 503 indicates the normal contact hole and 504 indicates the contact hole with a residue. In the graph, a resistance value of the normal contact hole 503 is low in the case of a forward bias (negative voltage) and is high in the case of a reverse bias (positive voltage). It is understood that, a breakdown occurs when 4V or higher is applied even in the case of the reverse bias, and the resistance value decreases. In this case, since the resistance value of the contact hole 504 having the residue is high, the difference between the resistance value of the normal portion and that of the defective portion is sufficiently large.

Figure 24:
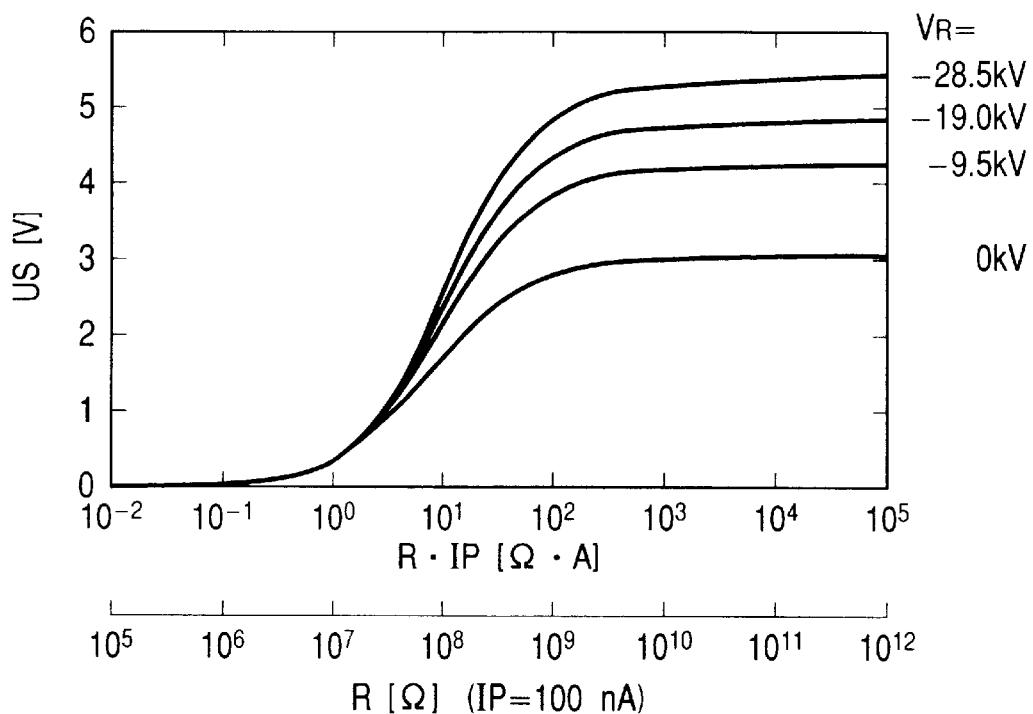
FIG. 24 is a diagram showing dependency on resistance of a charging voltage in the case where a retarding voltage is changed.

On the other hand, in the first embodiment, when the retarding voltage (or electric field near the wafer) is changed, dependency on resistance of the NSE changes as shown in FIG. 8, and it is understood that the resistance value measurement sensitivity can be changed. At this time, the charging voltage in the electron beam irradiated region changes as well. FIG. 24 shows the dependency on resistance of the charging voltage in the case where the retarding voltage VR is changed. An incident energy is 500 eV, the total electron emission efficiency is higher than 1, and the surface of a wafer is positively charged. It is understood that the charging voltage increases due to decrease in the retarding voltage VR (from 0 to −28.5 kV). The charging voltage in the case where the retarding voltage is 0V is about 3V at the maximum. Specifically, since the resistance value of the normal contact hole is sufficiently high, no leak current is occurs, the surface of the wafer is charged to a voltage about 3V, and the resistance value becomes about $10^{18}$ Ω. At this time, as understood from the right graph in FIG. 27, the number of emitted electrons is small, the voltage contrast image is dark, and the portion cannot be determined as a poor conduction portion. It is therefore considered that the voltage contrast image as shown in FIG. 26 is obtained as a result.

Figure 28:
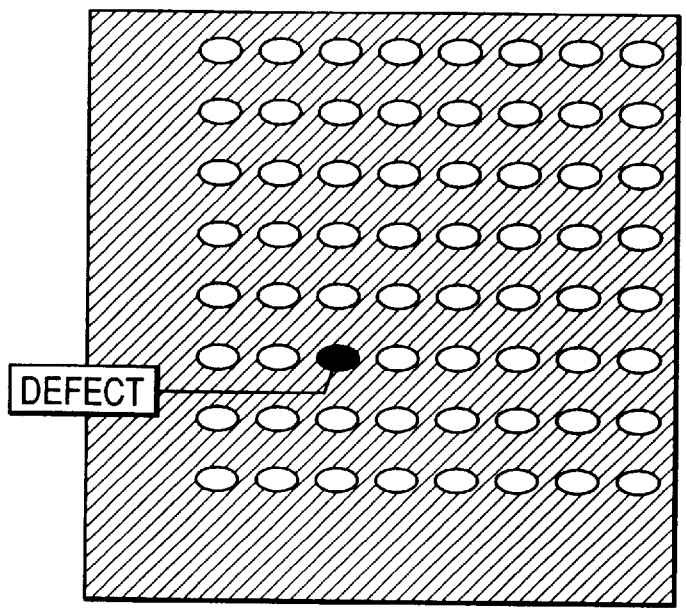
FIG. 28 is a diagram showing a voltage contrast image in the case where the retarding voltage is proper.

To enable an inspection to be conducted, a method of decreasing the resistance value of a pn junction by generating the charging voltage which is high enough to cause a breakdown in the pn junction is used. By setting the retarding voltage to −28.5 kV, the maximum charging voltage becomes 5V or higher (FIG. 24), it is expected that a breakdown occurs in the pn junction and the resistance value is sufficiently reduced ($10^8$ Ω or lower). Consequently, a difference occurs between the resistance value of the normal portion and the resistance value of the poor conduction portion. It is assumed from the right graph of FIG. 27 that the difference between their voltage contrast images (NSE) is sufficiently large, so that an inspection can be conducted. Practically, the retarding voltage was set to −28.5 kV and the voltage contrast image (FIG. 28) was obtained. As a result, a sufficient difference occurs between the voltage contrast image of the normal portion and that of the defective portion, and the defective portion can be displayed as a "defect" as in the second embodiment. In such a manner, the electron beam irradiation parameters can be determined from the dependency on resistance of the charging voltage and the electric characteristics of the circuit.

Figure 29:
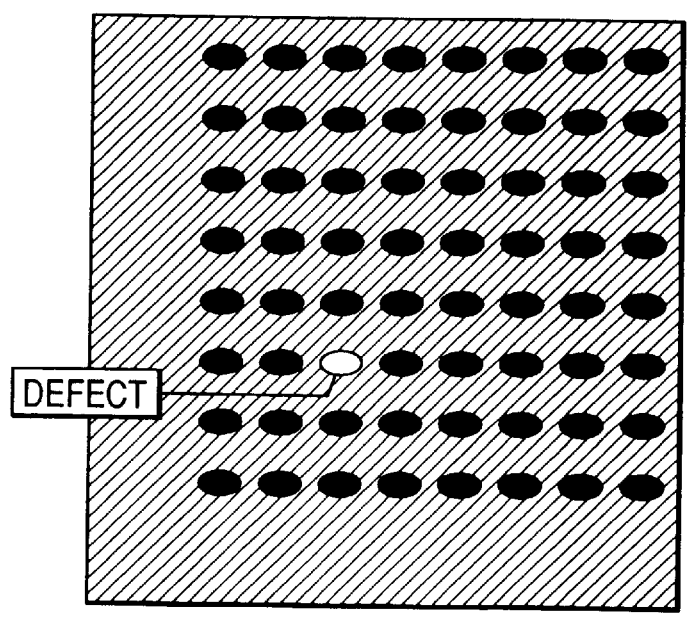
FIG. 29 is a diagram showing a voltage contrast image in the case where the retarding voltage is proper.

A wafer having a defect in a pn junction (without a residue) can be also inspected. An inspection example in the case where a breakdown occurs with a low charging voltage due to a defect such that the concentration of an n-diffusion layer in the pn junction is insufficient and a resistance value is consequently small will now be described. As indicated by 505 in FIG. 27, the resistance value is smaller than that of a normal portion. In this case, the inspection can be conducted with the retarding voltage of 0V. Since no breakdown occurs in the normal pn junction, the resistance value is sufficiently high and the voltage contrast image is dark. On the other hand, a breakdown occurs in the defective pn junction, the resistance is small, and the voltage contrast image is light. The obtained voltage contrast image is as shown in FIG. 29. The inspection parameters can be determined in such a manner.

Although the retarding voltage is changed in the above case, the purpose is to change the electric field around the wafer. Therefore, in place of changing the retarding voltage, by changing the position of an opposite electrode or peripheral electrode to change the electric field around the wafer, equivalent effects can be obtained.

Although the case where the retarding voltage is used as a parameter has been examined here, with respect to the other electron beam irradiation parameters (such as beam current, beam energy, and irradiation time) as well, optimum parameters depending on the characteristics of a sample exist.

Although an electron beam is used as a charged particle beam in the embodiments described above in detail, similar measurement can be made by using an ion beam in place of the electron beam.

As described above, according to the inspection method and system of the invention, in an inspection of a wafer partially completed such as a semiconductor device having a circuit pattern, the electric resistance and electric capacitance of a small region which cannot be measured by a conventional inspection system can be measured. By applying the invention to the wafer manufacturing process, the electric resistance and electric capacitance can be estimated. Consequently, a process of dealing with a failure can be performed immediately in the wafer manufacturing process. As a result, a fraction defective of semiconductor devices and other wafers is reduced and the productivity can be increased.

Since occurrence of an abnormal state can be immediately detected from the measurement, occurrence of a number of defects can be prevented. Further, as a result, the occurrence of defects can be reduced. Thus, the reliability of a semiconductor device or the like can be increased, an efficiency of development of a new product improves, and the manufacturing cost can be reduced.

What is claimed is:

1. An inspection method using charged particle beam, comprising:
    a step of scanning a region on a surface of a wafer in which an electric resistance value of a circuit pattern has dependency on voltage with a primary charged particle beam;
    a step of detecting signals of secondary electrons and back scattered electrons generated from said region which is irradiated with said primary charged particle beam;
    a step of forming an image of said region from the detected signals of said secondary electrons and back scattered electrons; and
    a step of analyzing a contrast of said image in the region irradiated with said primary charged particle beam on the basis of parameters of irradiating said primary charged particle beam and parameters of detecting secondary electrons and back scattering electrons, and determining absolute values of an electric resistance and an electric capacitance of said region.

2. An inspection method using charged particle beam, comprising:
    a step of scanning a first region on a surface of a wafer in which an electric resistance value of a circuit pattern has dependency on voltage with a primary charged particle beam;

a step of detecting signals of secondary electrons and back scattered electrons generated from said region which is irradiated with said primary charged particle beam;

a step of forming an image of said first region from the detected signals of said secondary electrons and back scattered electrons;

a step of scanning a second region on the surface of the wafer with a primary charged particle beam;

a step of detecting signals of secondary electrons and back scattered electrons generated from said second region which is irradiated with said primary charged particle beam;

a step of forming an image of said second region from the detected signals of said secondary electrons and back scattered electrons;

a step of determining absolute values of an electric resistance and an electric capacitance of each of said first and second regions from a contrast of an image corresponding to said first region and a contrast of an image corresponding to said second region;

a step of comparing the electric resistance and electric capacitance of said first region with that of said second region; and a step of determining whether a characteristic of a circuit pattern is good or not on the basis of a result of said comparison.

3. An inspection method using charged particle beam, comprising:

a step of scanning at least once a region on a surface of a wafer on which a predetermined pattern is formed with a primary charged particle beam;

a step of detecting signals of secondary electrons and back scattered electrons generated from said region which is irradiated with said primary charged particle beam in each scan;

a step of forming voltage contrast images from the detected signals of said secondary electrons and back scattered electrons; and a step of determining absolute values of an electric resistance and an electric capacitance in a desired region on said wafer surface on the basis of a change in said voltage contrast images.

4. An inspection method using charged particle beam, comprising:

a step of scanning a region on a surface of a wafer in which an electric resistance value of a circuit pattern has dependency on voltage with a primary charged particle beam;

a step of detecting signals of secondary electrons and back scattered electrons generated from said region which is irradiated with said primary charged particle beam;

a step of forming an image of said region from the detected signals of said secondary electrons and back scattered electrons;

a step of analyzing a contrast of said image in the region irradiated with said primary charged particle beam on the basis of parameters of irradiating said primary charged particle beam and parameters of detecting secondary electrons and back scattering electrons, and determining absolute values of an electric resistance and an electric capacitance of said region; and wherein the kind of a defective portion in said wafer is determined from the values of said electric resistance and electric capacitance.

5. The inspection method using charged particle beam according to claim 1, wherein said charged particle beam is an electron beam.

6. An inspection method using charged particle beam, comprising:

a step of scanning a region on a surface of a wafer in which an electric resistance value of a circuit pattern has dependency on voltage with a primary charged particle beam;

a step of detecting signals of secondary electrons and back scattered electrons generated from said region which is irradiated with said primary charged particle beam;

a step of forming an image of said region from the detected signals of said secondary electrons and back scattered electrons;

a step of analyzing a contrast of said image in the region irradiated with said primary charged particle beam on the basis of parameters of irradiating said primary charged particle beam and parameters of detecting secondary electrons and back scattering electrons, and determining absolute values of an electric resistance and an electric capacitance of said region;

wherein said charged particle beam is an electron beam; and wherein when said electric resistance is set as R, a current value IP of said electron beam lies within a range of $0 < \log(R \cdot IP) < 3$.

* * * * *